United States Patent [19]

Weber

[11] 4,166,720
[45] Sep. 4, 1979

[54] LEACHING COLUMN AND METHOD OF USE

[76] Inventor: Jerome B. Weber, 6300 Lewisand Ct., Raleigh, N.C. 27609

[21] Appl. No.: 798,824

[22] Filed: May 20, 1977

[51] Int. Cl.² ............................ G01N 31/06; G01N 33/24
[52] U.S. Cl. ................................ 23/230 R; 23/230.3; 47/66; 73/432 R; 422/101; 422/102; 422/261
[58] Field of Search ............... 23/272 SC, 292, 230 R, 23/272 R, 259; 210/31 C, 198 C; 423/658.5; 138/157, 169; 422/101, 102, 261

[56] References Cited

U.S. PATENT DOCUMENTS

| | | | |
|---|---|---|---|
| 381,871 | 4/1888 | Alexander | 138/169 |
| 1,437,937 | 12/1922 | Gray | 138/169 X |
| 2,487,574 | 11/1949 | Meng | 210/31 C |
| 2,733,135 | 1/1956 | Huckabay | 23/272 R |
| 3,334,973 | 8/1967 | Goren et al. | 23/272 X |
| 3,630,683 | 12/1971 | Robb | 23/292 X |
| 4,042,671 | 8/1977 | Bowdish | 23/272 R X |

FOREIGN PATENT DOCUMENTS

1086215 8/1960 Fed. Rep. of Germany ............ 261/97

OTHER PUBLICATIONS

Perry, "Chemical Engineers' Handbook, McGraw-Hill Book Co., fourth edition, 1963, pp. 18-32 through 18-35.

Primary Examiner—Arnold Turk
Attorney, Agent, or Firm—Mills & Coats

[57] ABSTRACT

A leaching column comprising two half cylinders held together by a removable band at one end and a leachate funnel at the other. For testing various pesticides and herbicides, the particular chemical is added to the leaching column and allowed it to pass through soil contained therein for a measured period of time. The half cylinders are then separated and, while retaining their respective soils, are used to perform a bioassay as well as chemical and radiological tests.

14 Claims, 10 Drawing Figures

U.S. Patent  Sep. 4, 1979  Sheet 1 of 2  4,166,720
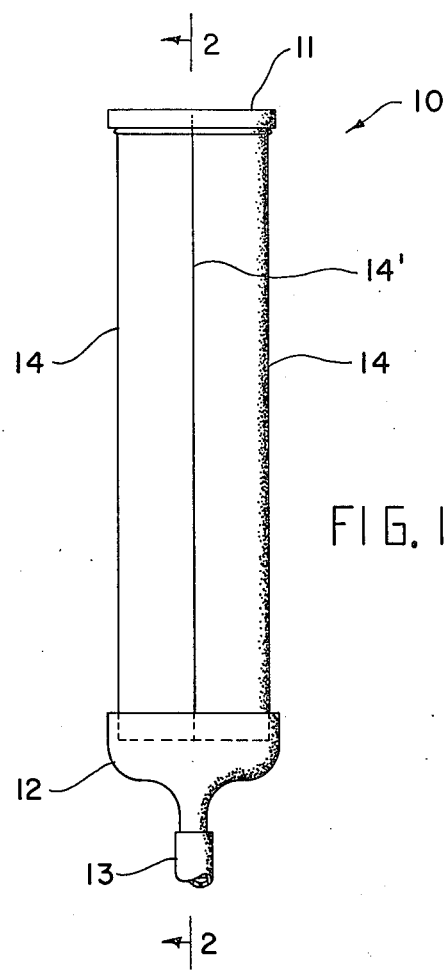
FIG. 1
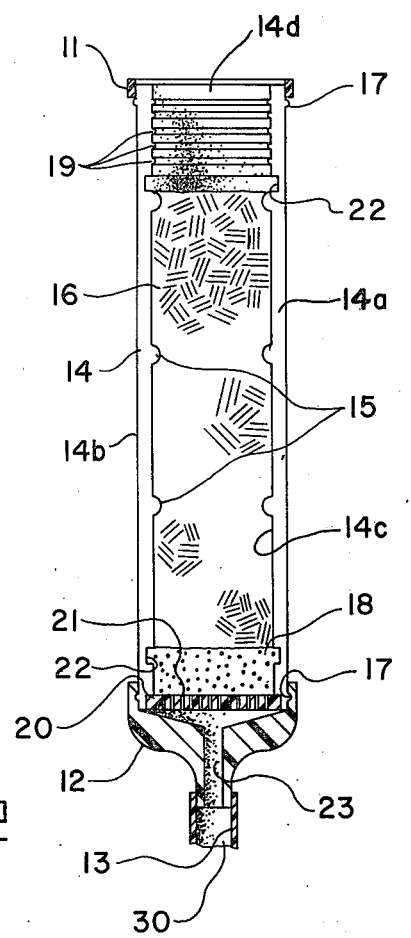
FIG. 2
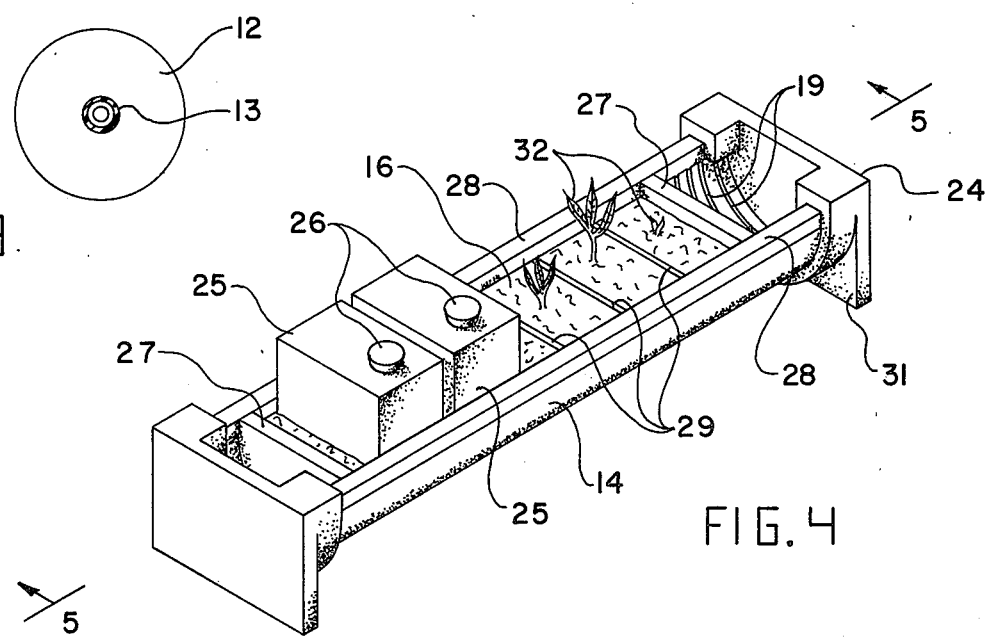
FIG. 3
FIG. 4

LEACHING COLUMN AND METHOD OF USE

The present invention relates to a pesticide and/or herbicide testing device and more particularly to a leaching column used in the performance of bioassays such that the soil penetration and active life of various chemicals used in agricultural soil treatments may be determined.

BACKGROUND OF THE INVENTION

In the distant past when farming was still in its infancy, little was done to a crop in the way of adding artificial growth stimuli. Even the simplest form of fertilizer (decaying organic matter) was not fully appreciated as an additive to increase yield.

As time passed, both population and land value increased. Therefore, simple economics dictated that a farmer had to somehow realize a greater yield per acre of land.

Science began to appreciate the needs of the agricultural world and began to investigate the entire spectrum of problems that had to be solved. First among these problems to be understood was the importance of fertilizer. Therefore, new and better fertilizers were developed for customized application to different crops. Next was the development of hybrids which were disease resistant and could withstand a greater range of weather conditions. In addition, other fields of endeavors were entered upon. They included weather forecasting, seed production, crop rotation, irrigation systems, pest control, weed control and many other pertinent areas.

Recently, in the areas of weed and pest control, much research has been undertaken with outstanding results being obtained. Herbicides and pesticides have been developed that virtually eliminate any and all weeds and pests. But, research goes on because newer and more effective chemicals are needed to replace those which become ineffective.

However beneficial these chemicals might be, not until recently has much been done to evaluate the adverse effects that various herbicides and pesticides have had on the environment. For example, DDT was a widely used pesticide that was found to retain its chemical composition for extended periods. The result being that it has lingered in the environment and produced harmful side effects on wildlife. Its use has since been halted. Other chemicals have been found to possess a very long active life thus creating and extending period of contaminating the environment.

The Environmental Protection Agency has been created by the federal government to monitor environmental changes and determine the causes of the same. In addition, this agency evaluates various consumer products, especially those that pertain to food and water, and removes such products from the market which are deemed harmful. Therefore, companies are now careful to put on the shelf only those products which they feel meet the guidelines drawn up by EPA.

It follows that before a company goes into full scale production of a particular product, it is going to test the product for any harmful side effects. It would be foolhardy to go through the expense of advertising and setting up distribution channels if the product could not be sold.

Different products require different types of tests. In the area of pesticides and herbicides it is considered very important to determine the leaching characteristics of each chemical in question. The reason for this being that each chemical has a different rate of being absorbed or leaching through soil and subsequently being deposited in the water table located below the ground. It is very important that the chemical does not leach down to this water table before its chemical composition has broken down. Therefore, tests were developed to simulate in a small scale what would occur in fields where the particular chemical was dispersed. As of the recent past the testing apparatus used is not common to all concerned parties. The outcome being that test results of identical chemicals may vary widely from one laboratory to the next.

Some laboratories have adapted a soda straw type leaching column as a testing device. When such a method is used the column is filled with soil to simulate a core sample. The chemical is then added to the top surface and caused to leach through when water is added. Any leachate which seeps through is collected at the lower end of the column and tested for the presence of the particular chemical. It follows that inconsistent results develop because each company has different control parameters such as various sized columns. Another undesirable feature of the soda straw type column is that it allows the water suspended chemical to flow down the interior walls of the column. Therefore, many times the leachate appears substantially more potent than the EPA would allow. There have even been instances where effective and reliable pesticides and herbicides have not been put on the market because of this inaccurate and non-standardized testing procedure.

SUMMARY OF THE INVENTION

The present invention presents a leaching column which is adapted to be used as a testing device for accurately evaluating leaching characteristics of various herbicides and pesticides. In addition, the present invention provides a simple, inexpensive leaching column that may be adapted as a standard for the testing of herbicides and pesticides.

It is therefore an object of the present invention to provide a leaching column which is adapted for testing the leaching characteristics of herbicides and pesticides through an earthen medium.

Another object of the present invention is to provide a leaching column which incorporates fluid dispersing ridges which direct the leachate so that it passes through the soil rather than flowing down the interior walls of the column.

A further object of the present invention is to provide a leaching column which is adapted to accept a funnel being removably attached about one end such that any leachate that passes through the column may be readily collected.

In addition another object of the present invention is to provide a leaching column which incorporates a final filter for retaining the soil disposed within the column while permitting any leachate to pass therethrough.

Another object of the present invention is to provide a leaching column which incorporates a graduated scale about its upper position such that any water added thereto may be easily measured.

An even further object of the present invention is to provide a leaching column which is cylindrically shaped and comprises two half cylinders separatably held together by a removably attached ring and funnel which are disposed about opposite ends of such column.

Another object of the present invention it to provide a leaching column which, after the leaching tests have been completed, may be used to perform a bioassay by disassembling the column and retaining the soil of each half cylinder within the same.

Another object of the present invention is to provide a leaching column which when broken down into its integral half cylinders may be adapted to perform both chemical and radiological tests on the soil contained therein.

Other objects and advantages of the present invention will become apparent from a study of the following description and the accompanying drawings which are merely illustrative of the present invention.

BRIEF DESCRIPTION OF THE DRAWINGS

FIG. 1 is a front elevational view of the leaching column of the present invention oriented in the normal testing position;

FIG. 2 is a cross sectional view of the present invention taken along lines 2—2 of FIG. 1;

FIG. 3 is a bottom plan view of the present invention;

FIG. 4 is a perspective view of the present invention illustrating a half cylinder being used for a bioassay;

DETAILED DESCRIPTION OF THE PREFERRED EMBODIMENT

Figure 5:
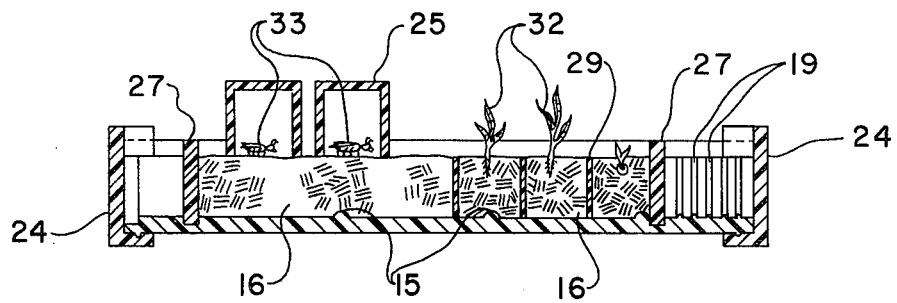
FIG. 5 is a cross sectional view of the present invention taken along lines 5—5 of FIG. 4.
Figure 6:
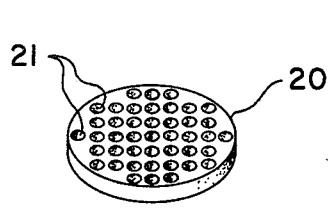
FIG. 6 is a perspective view of a filter used in the present invention.
Figure 7:
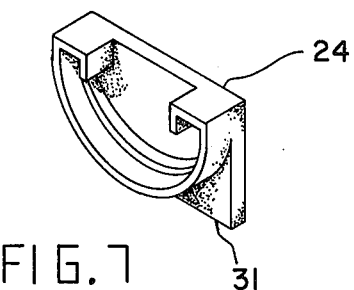
FIG. 7 is a perspective view of an end cap of the present invention.

With further reference to the drawings, particularly FIG. 1, a leaching column is shown therein and indicated generally by the numeral 10. Leaching column 10 is basically cylindrical in shape and vertically oriented when adapted for leaching tests. Comprising the main cylindrical body of the column are two half cylinders 14 which are held separably together at their uppermost ends by an externally disposed and removably attached ring 11. Half cylinders 14 are held separably together at their lowermost ends by an exteriorly disposed and removably attached funnel 12. A seal 14' is disposed between half cylinders 14 along their common surfaces 14a and 14b, two of which are shown in FIG. 2.

The interior of leaching column 10 is illustrated by FIG. 2, therein exposing a cross sectional view of the same as it would appear in normal testing. Protruding inwardly at the upper portion of each half cylinder 14 are a number of matching graduated scale ridges 19. Scale ridges 19 are adapted to be used to measure the volume of water added to the leaching column during testing. Disposed about the interior wall 14c of leaching column 10 and generally below graduated scale ridges 19 are a number of ring-like interiorly protruding dispersing ridges 15. Dispersing ridges 15 are incrementally spaced on wall 14c whereby the volume of various leaching mediums 16 may be readily measured during the filling of the column. In addition the primary function of dispersing ridges 15 is to direct any leachate which may be flowing along interior wall 14c back into the leaching medium 16 thereby facilitating accurate test results.

Disposed across the lower portion of the interior of leaching column 10 is a leachate filter 20 having openings 21 therein whereby the leaching medium 16 will be prevented from being carried out of the leaching column by any exiting leachate flow. Sand 18 can be provided adjacent filter 20 to further assure no undesirable loss of the leaching medium 16. Funnel 12 is disposed about the lower portion of leaching column 10. The funnel and its removably attached flexible tube 13 include interior passageways 23 and 30 respectively to channel any leachate, which exits leaching column 10, to a suitable container (not shown).

Illustrated in FIGS. 4 and 5 is a half cylinder 14 of the present invention being used to perform a bioassay. In this mode half cylinder 14 is horizontally oriented with its rounded side down. End caps 24 are removably attached to each end of the half cylinder to stabilize the same. Snap ridges 17 on each end of this half cylinder protrude radially outwardly and provide a locking means for the end caps 24.

Figure 8:
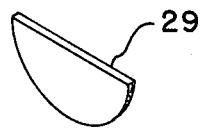
FIG. 8 is a perspective view of a soil divider of the present invention.
Figure 9:
FIG. 9 is a perspective view of a ring adapted for use on the present invention.
Figure 10:
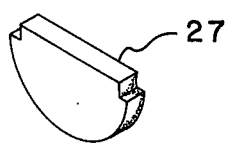
FIG. 10 is a perspective view of an end plate of the present invention.

Medium end caps 27, one of which is illustrated in FIG. 10, are inserted into medium end cap slots 22 disposed within interior wall 14c of half cylinders 14 such that the leaching medium is contained therebetween. Medium dividers 29 as illustrated in FIG. 8 are intermittently inserted into the leaching medium 16 thereby integrally separating several volumes of leaching medium one from the other.

Disposed adjacent surfaces 14a and 14b of half cylinders 14 and between end caps 24 are elongated rectangular side rails 28. Side rails 28 are sealed to surfaces 14a and 14b such that any water added to medium 16 during the bioassay will not overflow the same.

In the actual operation the leaching column of the present invention is initially prepared for the testing of various pesticides and herbicides. First the column is securely oriented in the vertical position with funnel 12 being downwardly disposed. Next a measured amount of quartz sand is poured into the interior opening 14d. Leaching medium 16 is then added in stratum layers such as those found in a particular core sample. A tapping of the column is continued throughout the filling of the column. This guarantees a uniform packing of the leaching medium used.

After the column has been filled to the desired level, the particular herbicide or pesticide to be tested is added to the topsoil in an amount relative to the cross sectional area of a field that the column represents. Water is then added until the level is aligned with the graduated scale ridge 19 desired. The medium is then allowed to leach for a determined period of time. During this leaching period the leachate is collected from the tube and retained for possible testing.

After time is allowed for draining the ring 11 and funnel 12 are removed from the column. The half columns are now separated by first separating the seal 14' and then pulling a thin wire down the entire length of the column. The half columns are then separated slowly such that each retains its respective medium. One half column may now be prepared to be bioassayed by attaching end caps 24 with leg like supports 31 formed thereon and inserting medium caps 27 and medium dividers 29. The other half cylinder may be used to supply samples for chemical and radiological analysis.

To perform the bioassay for herbicides, sensitive plants 32 are planted in the various medium units formed between the medium dividers 19. The medium dividers contain the root growth and prevent chemical seepage from one divided medium to another. The rate of plant growth and development within each particular divided medium is then monitored for any pertinent information that is deemed to be of value.

Pesticides are tested by inserting sensitive insects 33 into insect boxes 26 which are open at the bottom and disposed along the exposed soil. The conditions of a particular insect may be monitored by removing the insect box observation port stopper 26.

From these tests are leaching characteristics and effective chemical life of a particular pesticide or herbicide may be evaluated.

It is obvious therefore from the foregoing specification that the present invention provides a simple yet thorough apparatus and testing procedure for evaluating a particular chemical's leaching characteristics. It should also be appreciated that the present invention presents a device that can be adapted as a standard for evaluating leaching characteristics of various pesticides or herbicides.

The terms "upper", "lower", etc., have been used merely for the convenience of the foregoing specification and in the addended Claims to describe the material handling implement and its parts as oriented in the drawings. It is understood, however, that these terms are in no way limiting to the invention since the material handling implement may obviously be disposed in many different positions when in actual use.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range are intended to be embraced herein.

What is claimed is:

1. A device for use in determining the leaching characteristics of various substances comprising: an elongated, longitudinally separable leaching chamber having openings at each end thereof and containing a leaching medium whereby known substances can be placed in one end of said chamber and allowed to leach through said medium and exit the opposite end thereof prior to said chamber being longitudinally opened for substance analyzation of the basically undisturbed leaching medium; dispersing means disposed within said chamber for directing said substances away from the interior walls thereof and into said leaching medium whereby even distribution of said substance in said medium is obtained and flow of such substance along said interior walls is prevented; and medium dividers for use in each section when the same is separated to physically isolate the leaching medium into compartments.

2. The device of claim 1 wherein said chamber is generally cylindrical in shape.

3. The device of claim 1 wherein said leaching media is an earthen material.

4. The device of claim 1 wherein means are provided for supporting and stabilizing said chamber sections after they have been separated.

5. The device of claim 4 wherein said supporting and stabilizing means is at least one end cap.

6. The process for determining the leaching characteristics of various substances comprising: filling a chamber with a known volume of leaching medium; placing said substance in contact with said leaching medium; orienting said chamber to allow said substance to leach through said medium by gravity; directing said substance away from the interior walls of said chamber thereby aiding in the dispersion of said substance into said medium; collecting any of said substance which may leach completely 7. The process of claim 6 wherein said substance is a herbicide.

8. The process of claim 6 wherein said substance is a pesticide.

9. The process of claim 6 wherein said evaluating includes bioassaying of said medium.

10. The process of claim 6 wherein said evaluating includes radiological testing of said medium.

11. The process of claim 6 including integrally dividing and physically isolating said medium into compartment like divisions.

12. The process of claim 11 including placing of at least one plant in at least one of said divisions; and monitoring plant growth within said division.

13. The process of claim 11 including the placing of insects adjacent said medium in at least one of said divisions; and monitoring said insects relative to the effect of said substance thereon.

14. The process of claim 13 wherein said insects are confined adjacent said medium.

* * * * *